United States Patent [19]

Jeannotte et al.

[11] Patent Number: 5,007,740
[45] Date of Patent: Apr. 16, 1991

[54] OPTICAL PROBE FOR FLUID LIGHT TRANSMISSION PROPERTIES

[75] Inventors: Anthony C. Jeannotte; Anthony C. Gilby, both of Foxboro, Mass.

[73] Assignee: The Foxboro Company, Foxboro, Mass.

[21] Appl. No.: 330,533

[22] Filed: Mar. 30, 1989

[51] Int. Cl.[5] .......................... G01N 21/00; G01N 1/10
[52] U.S. Cl. .................................... 356/436; 350/246; 350/338; 250/576
[58] Field of Search ................... 356/435–436, 356/439, 409, 440, 442, 244, 441, 443, 246, 338; 250/576

[56] References Cited

U.S. PATENT DOCUMENTS

| | | | |
|---|---|---|---|
| Re. 30,391 | 9/1980 | Liston | 356/409 |
| 2,203,720 | 6/1940 | Dale | 356/436 |
| 4,171,909 | 10/1979 | Kramer et al. | 356/436 |
| 4,534,651 | 8/1985 | Minikane | 356/440 |
| 4,730,882 | 3/1988 | Messerschmidt | 350/96.1 |
| 4,851,665 | 7/1989 | Pesavento et al. | 356/436 |
| 4,876,069 | 10/1989 | Jochimsen | 356/442 |

OTHER PUBLICATIONS

"Nouvelle Optode Passive Pour La Spectrofluorimetrie et La Spectrometrie Raman", Gilbert Boisde, Barbara Kirsch, Patrick Mauchien, and Stephane Rougeault; Paper Presented at Opto 88, 17–19 May, 1988, published in the Proceedings Opto 88 at pp. 294–299.

"Aspects of Optical Fibers and Spectrophotometric Sensors in Chemical Process and Industrial Environments", Gilbert Boisde and Jean-Jacques Perez; Paper Presented at ECO1, 22–23 Sept., 1988, Hamburg, GFR, Published at SPIE, vol. 1012 In-Process Measurements, 1988, pp. 58–65.

Primary Examiner—Richard A. Rosenberger
Assistant Examiner—Hoa Pham
Attorney, Agent, or Firm—Terrence Martin; Jules J. Morris

[57] ABSTRACT

In accordance with the present invention, radiant energy is transmitted to a probe element including an interior conical reflecting surface and a fluid sample chamber. Portions of the light which have been transmitted, partially attenuated, or scattered by a fluid sample in the sample chamber are directed by at least a portion of the interior conical reflecting surface to a location for collection of the transmitted, partially attenuated, or scattered light. A stilling valve incorporated into the probe element enables elimination of entrained gas bubbles from the chamber.

45 Claims, 8 Drawing Sheets

OPTICAL PROBE FOR FLUID LIGHT TRANSMISSION PROPERTIES

TECHNICAL FIELD

This invention relates to optical probes for sensing fluid characteristics optically, and particularly to optical analysis of a fluid sample in a sample chamber. More particularly, the present invention is directed to a combination optical probe and stilling well for optical sampling of a fluid admitted to a sample chamber.

BACKGROUND OF THE INVENTION

As the advantages of fiber optic based communication and control of industrial processes becomes better known, increasing emphasis is being placed on various methods of simple, inexpensive, and reliable communication of optically sensed physical parameters, or measurands. Optical analysis of certain fluid materials offers known improvements over other techniques.

The measurement of the light transmitting or light scattering properties of a fluid ordinarily requires that a beam of light or radiant energy be passed through the fluid and subsequently directed towards a radiant energy detector. Optical apparatus for accomplishing this task have been used in which discrete components such as lenses, mirrors, or internally reflecting light guides are employed for the sampling apparatus. Optical fibers may be used to convey the light to the sensing apparatus and back to detection equipment. Examples of such techniques are illustrated in U.S. Pat. Nos. 4,591,268 to Lew ('268); 4,320,978 to Sato ('978); and 4,152,070 to Kushner et al ('070). These methods are generally unsuited for direct submersion within the test fluid because the optical surfaces are derogated by fluid contact, i.e., dirt erosion, pitting, and dissolving of the surfaces.

The use of fiber optic light guides is recognized for permitting the measurement of the light transmitting or scattering properties of fluids in harsh environments, such as a process container or pipeline containing the fluid of interest. Thus, U.S. Pat. Nos. 4,040,743 to Villaume et al ('743) and 4,561,779 to Nagamune et al ('779) depict apparatus for the in-situ measurement of fluid suspensions. A similar approach described by H. Raab in *Technisches Messen*, 50, 1983(12), p. 475, is employed for the in-situ assay of certain fluids. A common feature of these known methods is the use of relatively small prisms having planar surfaces which act to bend a light beam through 90 degrees. Such prisms can be expensive to fabricate and difficult to align.

Conical reflecting elements have been previously described in the literature (cf. M. Rioux, et al, *Applied Optics*, 17(10), 1978, p. 1532). Their use has been primarily as imaging devices for objects disposed along the conical reflecting element's axis of revolution. As will become evident from the subsequent disclosure, the method and apparatus of the invention described herein depart from these known configurations and permit utilization of the interior conical reflecting surface in an off-axis manner.

In addition, since the present invention has application in the fermentation arts, it is useful and often necessary to minimize bubbles in the measurement area. Known passive bubble reducing techniques are inadequate when applied to a fermentor environment. Typically intricate and narrow passageways designed to promote drainage of foamy samples are ineffective, and may be prone to blockage from the solution, which is typically cell-laden. For this reason, the present invention comprehends the inclusion of a valved still well or stilling chamber from which the bubbles and foam are effectively drained prior to measurement. The combination probe thus incorporates a stilling well chamber, which may be either electrically or pneumatically valved, and a novel optical probe. Such a valved still well embodiment includes an 'open' position in which the solution is free to pass through the measurement chamber, and a 'closed' position in which the bubbles and/or foam in the solution are permitted to drain briefly before the measurement.

For the purposes of this limited description, "fiber optic", "optical fiber", "light guide", and "radiant energy pathway" refer to optical communication paths, generally optical fibers. As used herein, the terms "radiant energy" and "light" are used interchangeably to refer to electromagnetic radiation of wavelengths between $1 \times 10^{-7}$ m and $1 \times 10^{-4}$ m, and specifically includes infrared, visible, and ultraviolet light. For simplicity, such electromagnetic radiation may be referred to as simply "light." These terms specifically include both coherent and non-coherent optical power. "Monochromatic" refers to radiant energy composed substantially of a single wavelength. "Collimated" light refers to radiant power having rays which are rendered substantially parallel to a certain line or direction.

SUMMARY OF THE INVENTION

It is an object of this invention to provide improved apparatus for the introduction and collection of radiant energy into, through, and from a sample chamber.

Another object of the invention is the incorporation of a stilling mechanism to rapidly and effectively eliminate bubbles and/or foam in a fluid sample at the time of the measurement.

Further objectives include provision of methods and apparatus which are both cost-effective and capable of withstanding harsh process conditions.

A further object of the present invention is that it is to be easily and inexpensively manufactured.

The probe of the present invention is directed to using an interior conical reflecting surface to direct radiant energy into and out of a sample chamber. The apparatus of the present invention can utilize the conical reflecting surface off-axis. The invention broadly includes opto-mechanical components which carry light from a radiant energy source to a sample chamber, direct this light into the chamber containing a test fluid sample, and collect and redirect light which has been transmitted, partially attenuated or scattered by the sample towards a radiant energy detector.

The probe uses optical methods and apparatus for simplified remote measurement of the light transmitting or light scattering properties of a fluid, especially when it is necessary to confine the fluid to its natural process vessel, a pipe, or where environmental factors such as excessive temperature preclude the possibility of siting light sources or detectors in the immediate vicinity of the fluid. The invention facilitates measurement of fluid properties over a broad range of applications, including but not limited to the determination of dissolved impurity levels in process fluids, the turbidity of fluids such as the undissolved solids content of fermentation systems or particle sizing. Other measurements include filter bed breakthrough, water quality, carbon dioxide in beverages, sugar in organics, water in gasoline, methanol in gasoline, sulfates and phosphates in water, gaseous analysis and the like.

The method and apparatus of the present invention are broadly directed to opto-mechanical components which carry light from a radiant energy source to a sample chamber containing a test fluid of interest, direct this light into the sample chamber and collect and redirect the light which has been transmitted, partially attenuated, or scattered towards a radiant energy detector.

More particularly, the apparatus is a probe for optically sampling a fluid in a test or sample chamber, which apparatus includes a source of radiant energy, an interior conical reflecting surface segment surrounding part of a sample chamber, a first portion of which reflecting surface is used for directing radiant energy through the sample chamber, another portion of the conical reflecting surface is used for collecting radiant energy from said chamber, a first pathway for conveying radiant energy to the first portion of the conical reflecting surface, and a second pathway for conveying radiant energy away from said sample chamber, via another portion or other portions of the reflecting surface, to a detector.

A feature of the present apparatus is the use of an interior conical reflecting surface to direct radiant energy into and out of the sample chamber. The conical reflector segment permits rapid, economical assembly and alignment of the optical elements, and improves the efficiency with which the light is transferred into and from the sample chamber.

Measurement of fermentation characteristics and fluids containing bubbles or foam which would obscure the measurement is facilitated by incorporating stilling apparatus in the probe design to enable elimination of such bubbles and/or foam in order to enable accurate measurement of the desired solution characteristic. This aspect of the present invention therefore includes a sample chamber (which may be longitudinally oriented) having at least one upper vent port, one or more lower side drain ports, and valve means to close the lower side drain port or ports. The valve may be either pneumatically or electrically operated; electric operation is preferred.

BRIEF DESCRIPTION OF THE DRAWING FIGURES

Numerous other features and advantages of the invention disclosed herein will be apparent upon examination of the several drawing figures forming a part hereof. Solid line arrows may be used to indicate light rays. In all views, like reference characters indicate corresponding parts or elements.

DETAILED DESCRIPTION OF THE PREFERRED EMBODIMENT

FIGS. 1, 4, 5, and 6 illustrate a preferred embodiment of the present invention in which a probe 10 incorporating an interior conical reflector segment 11 is joined to a lower stilling valve actuator segment 12, to an upper main body segment 14 having an upper vent hole 15, and which in turn is joined to an extension tube segment 16. The probe 10 includes an axis of revolution 13 of the conical reflector segment 11 which, extended, may be the center line of the probe 10. The axis of revolution, of course, need not necessarily be the probe center line.

Figure 1:
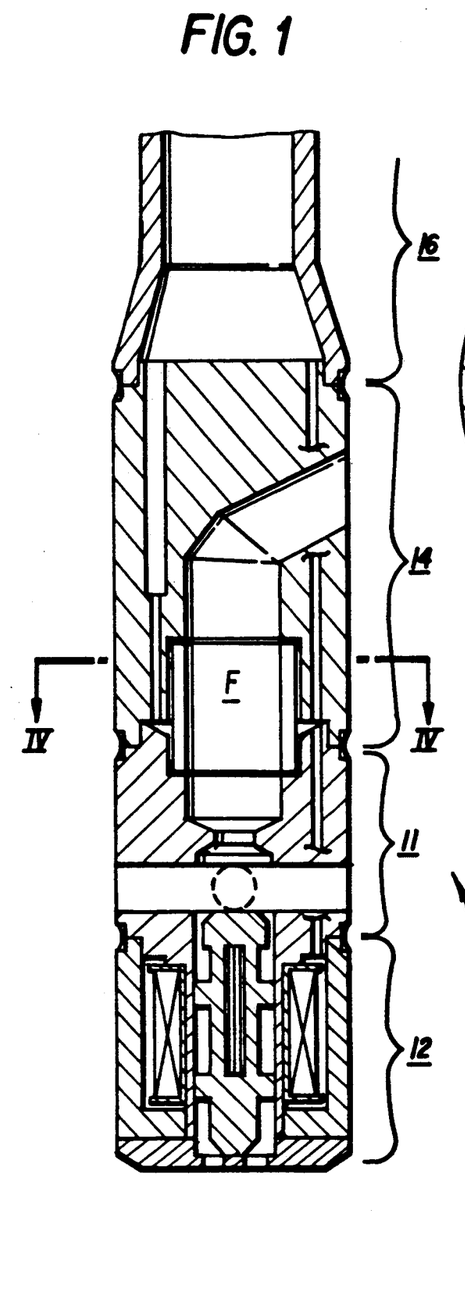
FIG. 1 illustrates in cross-sectional view major portions of an optical probe according to a primary aspect of this invention.

The interior conical reflector segment 11 is made by forming an interior conical reflecting surface 17 into the central area of a (preferably thickwalled and hollow) cylindrical body. An interior conical reflecting surface 17 of reflector segment 11 is easily fabricated by a simple cutting operation on a lathe. A quality reflecting surface 17 is obtained either by fine cutting of the reflecting surface 17 followed by a finish polish or by other well-known optical surface-finishing methods. A reflective overcoat (not shown) can be deposited to further improve the reflectivity of the reflecting surface 17. It will be appreciated by those skilled in the art that the light transmission and reflection properties of the optical elements described here will be influenced by the wavelength or wavelengths of light used to make the sample measurement, e.g., the light scattering or light transmitting properties of the sample fluid. Further, the probe 10 reflector and main body segments 11, 14 may be exposed to the process fluid (F) and therefore must be chosen so as to withstand the chemical and physical properties of their expected environment.

The probe 10 segments 11, 12, 14, 16 are essentially elongated and cylindrical in shape, though another shape may be used. The reflector segment 11 incorporates an interior conical reflecting surface 17; the segments 11, 14, 16 house the optical, electrical (or pneumatic) and mechanical components which carry light from a remotely located radiant energy source (not shown) to a sample chamber 18 containing a test fluid (F). Sample chamber 18 is formed in the central area joining the segments 11 and 14. A cylindrical, transparent section of glass, having a hollow, longitudinal central portion is used. The sample chamber 18 extends from above the juncture of the segments 11, 14 to a point below the conical reflecting surface 17 within the reflector segment 11. A probe 10 central passageway 38 extends above and below the sample chamber 18 in the segments 14, 11 respectively.

A plurality of longitudinal passages such as the light guide passages 28 provide access and protection for the light guides 20, 21, 26 entering through the segments 11, 14 and portions of the segments 12, 16. These passageways 28 additionally provide for precise alignment of the light guides 20, 21, 26 at the desired radial angle and radial distance from the centerline of the segment 14 corresponding to the axis of revolution 13 of the reflector segment 11. Wires (not shown) communicate electrical power needed to actuate the valve mechanism via passageway 29. Pneumatic communicating passageways may be substituted as appropriate.

The segments 14, 16 may be joined in a sealing manner as is known to those of skill in the art, including welding or by adhesives. The use of concentric, stepped counterbores on the segments 14, 16 facilitate mechanical alignment of the segments.

Figure 6:
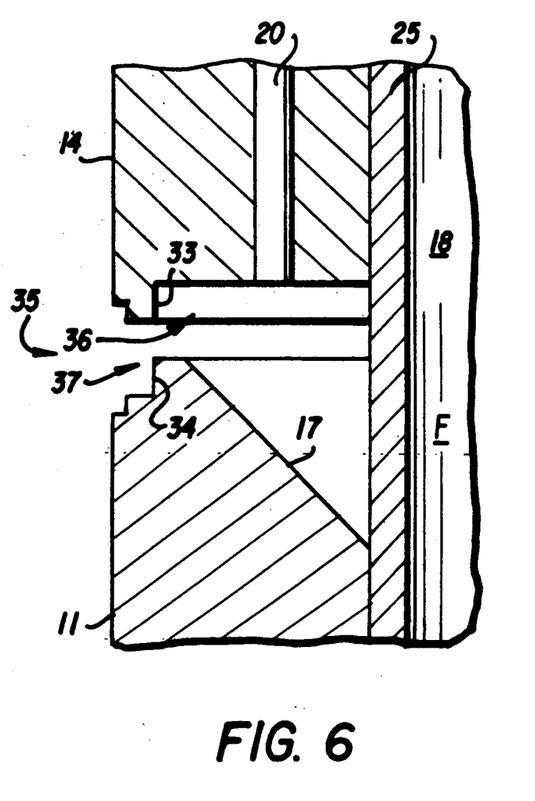
FIG. 6 illustrates a detail of the device of FIG. 5.

Similarly, the segments 11, 14 may be joined by concentric, stepped counterbore features (as are more clearly shown in detail FIG. 6). Attachment of the interior conical reflector segment 11 to the upper main body segment 14 may be effected by a circumferential weld. The sample chamber 18 has a transparent wall 25 disposed between the conical reflector segment 11 and the upper main body segment 14. Prior to joining, the transparent wall 25 (which is a cylindrical section and formed of a strong transparent material such as high strength, high temperature glass), is inserted centrally of these two segments (11, 14) which are then held together with a pressure force suitable for compressing circular or O-ring seals 31, 32 to the desired state of compression for effecting sealing against leakage of the sample fluid. Axial alignment of the reflector segment 11 and the main body segment 14 is accomplished by the mating surfaces 33 and 34 which consist of a stepped counterbore 35 fitted with the main body segment 14 bore 36, the internal diameter of which is no smaller than the external diameter of the step 37 machined into the outside diameter of the reflector segment 11. This mating configuration shown is for illustration only and is not intended to be a limitation of the appended claims, as other equally convenient configurations for aligning and joining the segments known to those of skill in the art may be substituted.

Figure 4:
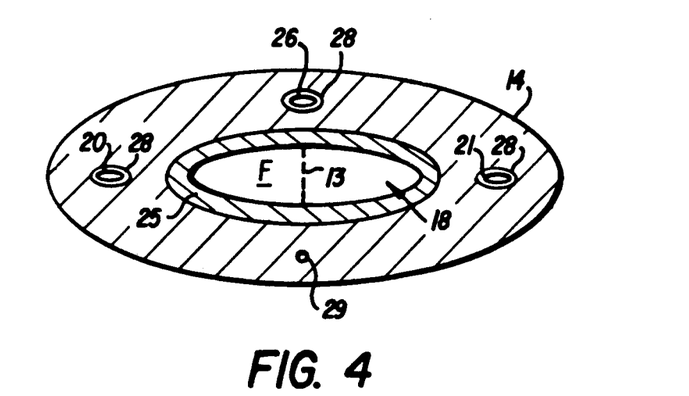
FIG. 4 illustrates a transverse section of the invention, taken immediately below the top seal of the sample chamber, as indicated in FIG. 1.

FIG. 4 reveals the interior section of upper main body segment 14 near the top of sample chamber 18, showing the centerline of segment 14, which is also the axis of revolution 13 of the interior conical reflector segment 11. The first, second, and additional light guides 20, 21, 26 pass through this section. The cylindrical transparent wall 25 forming the sample chamber 18 within the segment 14 includes a plurality of light guide passageways (shown enlarged for emphasis only) 28 surrounding light guides 20, 21, 26 through the segment 14. A further passageway 29 surrounding the electrical/pneumatic communicating passageway to stilling valve actuator segment 12 (not shown in this view) bears the necessary actuation control lines to the stilling valve segment 12.

Figure 5:
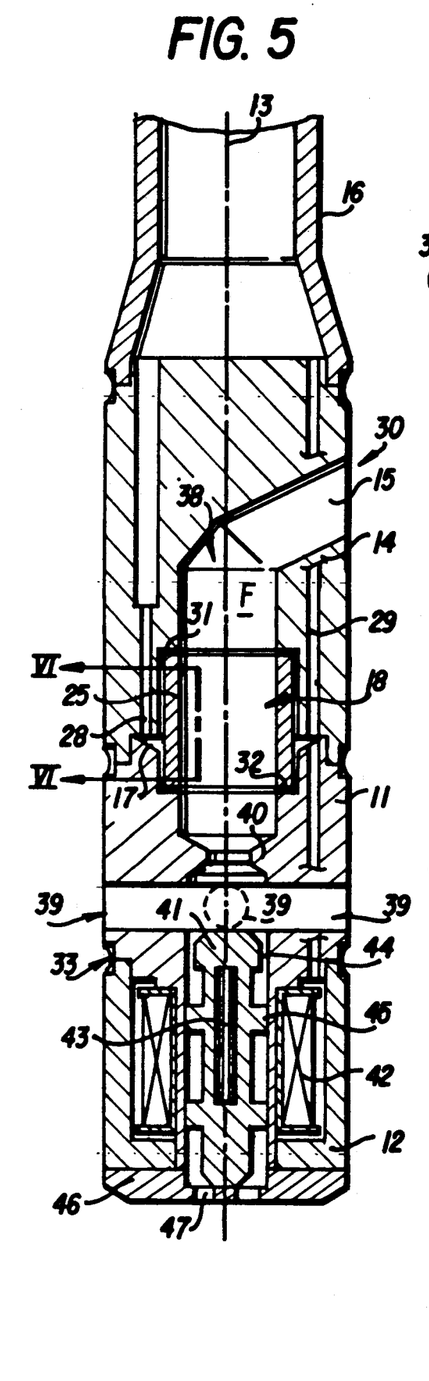
FIG. 5 illustrates a longitudinal section of the invention shown in FIG. 1, further illustrating details of the device.

Turning now to FIG. 5, the reflecting properties and cylindrical symmetry of the conical reflecting surface 17 enable rapid, simple, and comparatively inexpensive manufacture of the novel measurement probe 10 reflector and main body segments 11, 14 incorporating this reflecting surface 17. The segments 11, 12, 14, 16 are disposed along a longitudinal axis which serves as the axis of revolution 13 of the reflector segment 11; an upper vent hole 15 extends upward from the sample chamber 18, defined by a transparent wall section 25, and communicates to the upper port 30, where the sample fluid (F) freely exits from one side of the main body segment 14 above the sample chamber 18. While this embodiment is illustrated by a single such upper port 30, a plurality of such ports may also be employed.

The reflector segment 11 contains one or more process fluid (F) lower ports 39. The lower ports 39 communicate the process fluid (F) directly through the central passageway 38 thence to the upper port 30.

In a preferred embodiment, the reflector segment 11 includes in its lower end certain portions of a valving apparatus which permit the sample chamber 18 to intermittently function as a novel still well as well. More particularly, there is formed in the lower end of the reflector segment 11 a valve seat or stop 40, in the form of a constriction in the cross sectional diameter of the central passageway 38 in the reflector segment 11. The valve stop 40 enables interruption of the free communication of process fluids (F) from the lower port or ports 39 through the sample chamber 18 to the upper port 30 via a vent 15.

A stilling valve actuator segment 12 is responsible for closing the stilling valve formed by the valve seat or stop 40 in the reflector segment 11 and by a plunger 41, which is located in the central passageway of the actuator segment 12. The plunger is sealingly shaped to join with the stop 40 and thus close central passageway 38. Power for actuating the plunger 41 is shown in this example as electromagnetic via a solenoid coil 42; pneumatic drive means may be substituted such that the plunger 41 closes with the stop 40 by pneumatic pressure. Solenoid coil 42 coacts magnetically with a permanent magnet 43 embedded in the plunger 41, causing the plunger 41 to close the central passageway 38 at the valve stop 40. The plunger 41 preferably includes a plurality of arcuate ridges 44, 45 to ensure proper coaxial alignment of the plunger 41 with respect to valve stop restriction 40. Wires (not shown) communicate the electrical power to actuate the valve mechanism 40, 41 via the coil 42.

The valve actuator segment 12 may be attached to the reflector segment 11 in a manner substantially similar to that in which the reflector segment 11 is joined to the main body segment 14, previously described.

The plunger 41 is retained within the actuator segment 12 by placement of a bottom cover 46 over the lower end of the actuator segment 12; one or more process fluid drain holes 47 may be included in the bottom cover 46 to permit essential drainage and to avoid hydraulic restriction on the free movement of the plunger 41 to close the valve plunger 41 to seat 40.

Figure 2:
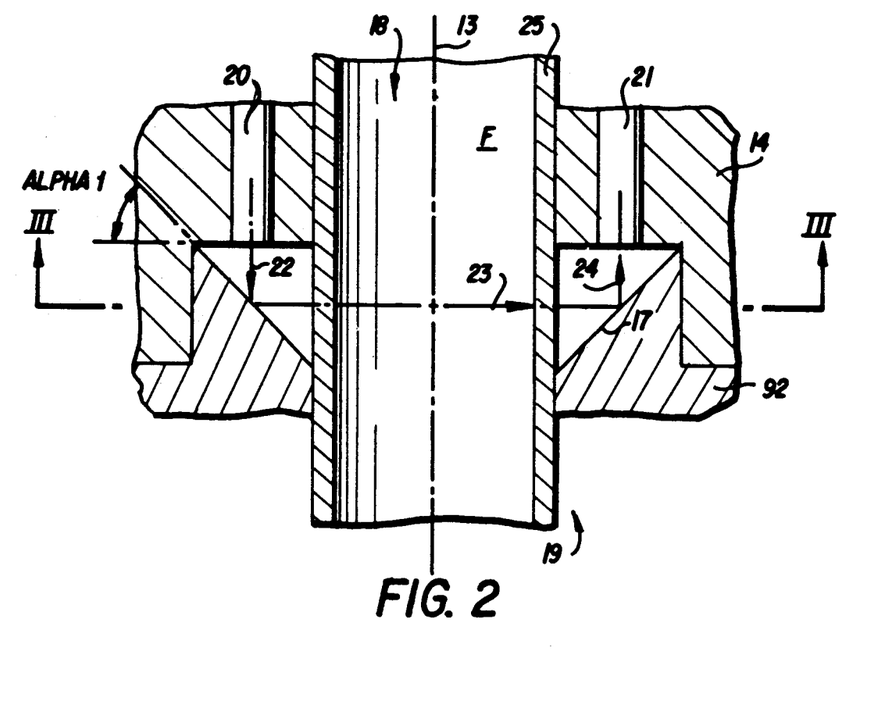
FIG. 2 illustrates in cross-sectional view portions of another optical probe according to a primary aspect of this invention.
Figure 3:
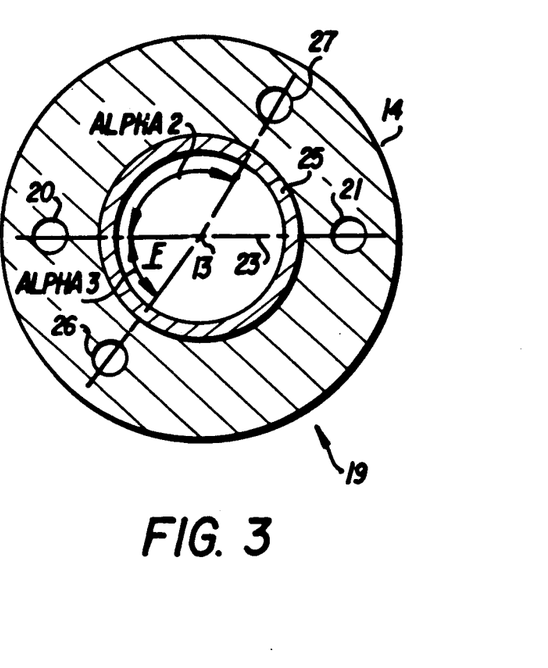
FIG. 3 illustrates an optical probe assembly according to another aspect of the present invention.

A simplified reflector segment is shown in FIGS. 2 and 3. The more basic probe 19 (FIG. 2) having a similar reflector segment 92, the inclination angle alpha 1 of the conical reflecting surface 17 is about 45 degrees in the preferred embodiment. The main body segment 14 houses optical light guides 20, 21, 26. The light guides 20, 21, 26 extend along the length of the main body segment 14, being terminated in close proximity to the reflecting surface 17. Additional light guides 26, 27 may be disposed at various angles relative light guide 20.

A detailed description of the reflector segment 92 relating to light reflecting characteristics of the reflective surface 17 follows, illustrating optical operation of the generic optical probe 19 according to the present invention. Light from a remote source (not shown) is communicated to the probe 19 via a first optical fiber 20. The fiber 20 is positioned in and by the passageway 28 (FIG. 4) in the main body segment 14 and is terminated adjacent the conical reflective surface 17. The conical reflective surface 17 directs this light into and through sample chamber 18, and collects and redirects the light which has been transmitted, partially attenuated, or scattered. Other optical fibers such as the fiber 21 convey the light towards a remotely located radiant energy detector (not shown). Additional fibers 26, 27 may be positioned off-axis to receive light.

A ray of light traveling along the optical axis of this system, originating in the light guide 20 and transmitted to the light guide 21 is composed of a series of light ray segments 22, 23, 24 for the conical reflector segment 92 having a reflecting surface 17 and an inclination angle of about 45 degrees. The initial light ray portion 22 represents that portion of the light ray leaving light guide 20 and incident on a first surface area of the reflecting surface 17 while the sampling light ray 23 denotes that light ray portion which is reflected through an angle of about 90 degrees and passed through a section of the sample chamber 18 transparent wall 25, where the light sampling ray 23 encounters the test sample fluid (F).

After being passed through the sample fluid (F) and the opposite sample chamber 18 wall 25, the sample ray 23 encounters a second surface portion of reflecting surface 17 and is again deflected through an angle of about 90 degrees to form an exit light ray 24. The light ray segment 24 represents a continuation of the ray 23 from the second portion of reflecting surface 17 to and incident upon light guide 21. FIG. 3 shows the apparatus of FIG. 2 in the plane which contains the light ray segment 23 and which is perpendicular to the axis of revolution 13 of the conical reflector segment 92.

The additional light guides 26, 27 can serve either as collectors of light originating from guide 20 or they can function as light conduits for other external light sources when such are required. The additional light guides 26, 27 receive light scattered substantially from the center of sample chamber 18. If the angle alpha 2 is 90 degrees, the configuration is termed nephelometric and the probe may advantageously be used as a nephelometric turbidity probe. The additional light guide 26 collects that light originating from the light guide 20 which light is subsequently scattered by the test fluid (F). In combination, the light guides 20 and 21 permit the measurement of either the forward-scattering component of the turbid media or the attenuation of radiant energy as a function of the number density of dissolved materials in an otherwise homogenous fluid.

Figure 7:
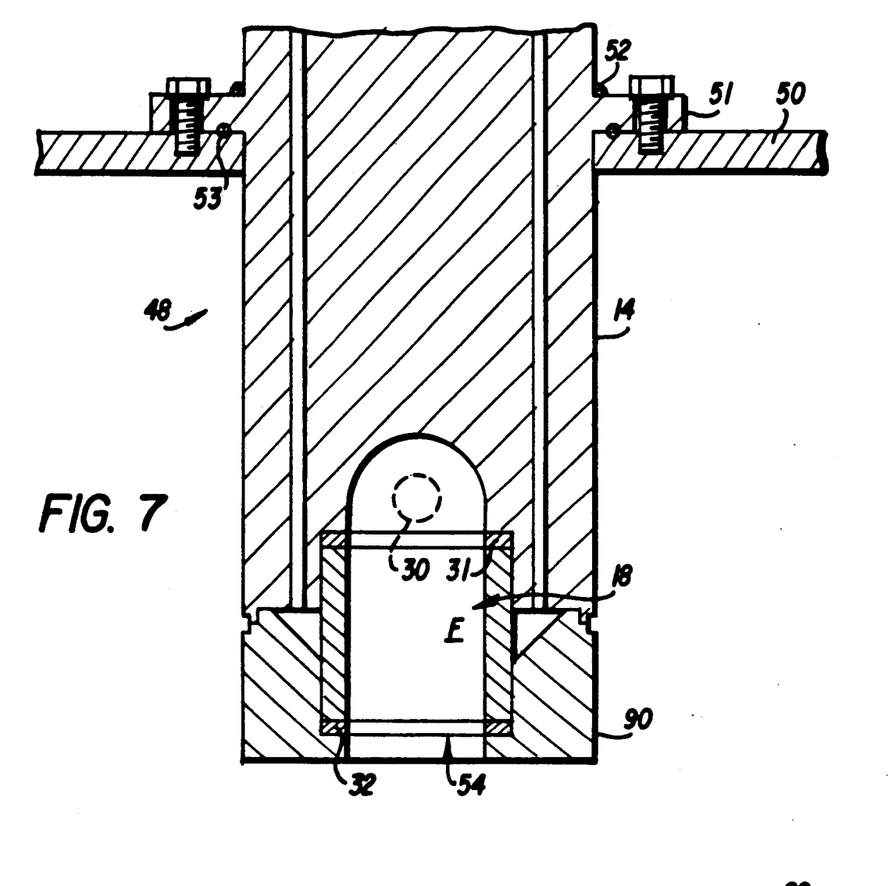
FIG. 7 illustrates a longitudinal section of the invention shown in FIG. 2, wherein the probe is permanently mounted.

Several alternative embodiments of an optical probe using the conical refelective surface are shown in FIGS. 7 through 15. The simplified optical probe 48 of FIG. 7 is adapted for permanent mounting on a vessel, such as a storage tank or process vessel 50, only a portion of which is shown. A peripheral flange 51, attached to the probe 48 (as for example, by a circumferential weld 52) illustrates how the probe 48 may be secured to the process vessel 50. A simplified probe similar to the probe 92 shown in FIG. 2 is illustrated. The process vessel 50 may, for example, be a container of fixed size or a pipeline, which can accommodate the length of the probe 48 exposed to the process fluid (F). A sealing means, such as a circular or O-ring seal 53 can be used to prevent the fluid (F) from leaking to the outside environment.

Alternatives for effecting such seals are known to those skilled in the art; the O-ring of this embodiment is not limiting and does not preclude the use of alternative seals. An adequate seal between the sample chamber 18, the reflector segment 90, and the main body 14 may be accomplished with the aid of two O-ring seals 31, 32, glass-to-metal graded seals or the like. These elements may be joined and sealed as previously described. The process fluid (F) is permitted to flow freely through the sample chamber 18 via a lower port 54 and one or more upper ports 30. The measurement process is as previously described; it may be continuous or intermittent with the addition of still well valving apparatus.

Figure 8:
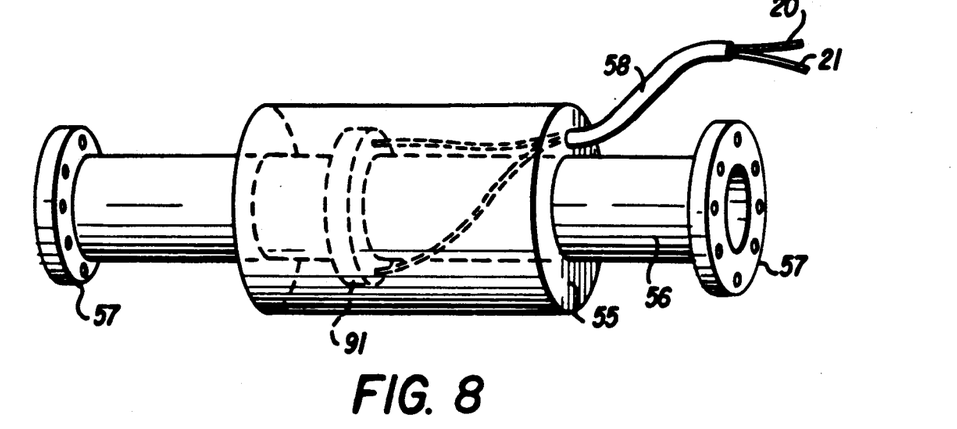
FIG. 8 illustrates the invention shown in FIG. 2, wherein the probe is permanently mounted circumjacent a pipe which may be flanged for insertion in a line.

FIG. 8 depicts another embodiment of the invention. An optical sampling apparatus includes a probe body 55 which contains the conical reflector segment 91 and the light guides 20, 21. It is configured such that the conical reflector segment 91 fits over a pipe section 56 (at least a portion of which is transparent at the sample chamber site) which can in turn be coupled to a sample line (not shown) by one or more end flanges 57. In this embodiment, a single service cable 58 contains all of the optical light guides 20, 21.

Referring briefly again generally to FIGS. 2 and 3, light leaving the light guide 20 includes light rays whose maximum inclination angle with respect to initial light ray portion 22 are determined by the numerical aperture of the light guide 20; all rays having inclination angles less than this maximum inclination angle define an acceptance cone of light which may be transmitted into the light guide 21. Because of this, the plurality of rays striking the reflection surface 17 will result in skew rays through the sample chamber 18, not all of which skew rays will fall within the acceptance cone of the light guide 21 after deflection from the reflecting surface 17 upon exiting the sample chamber 18. This circumstance reduces the maximum radiant energy which traverses the sample chamber. In certain applications, such loss of radiant energy is not serious since one can choose among available light sources, light guides, and radiant energy detectors, the accumulated sensitivities and losses of which, when combined, yield a favorable measurement sensitivity.

A further improvement of the embodiment of the invention depicted in FIGS. 2 and 3 addresses the decreased measurement sensitivity situation described above; the optical scheme of FIG. 9 promotes more efficient transfer of light through the sample chamber 18. Additionally, this embodiment results in optical rays the passage of which through a test fluid (F) is affected less by changes in the refractive index of the fluid, such as might result from changes in temperature for example.

Figure 9:
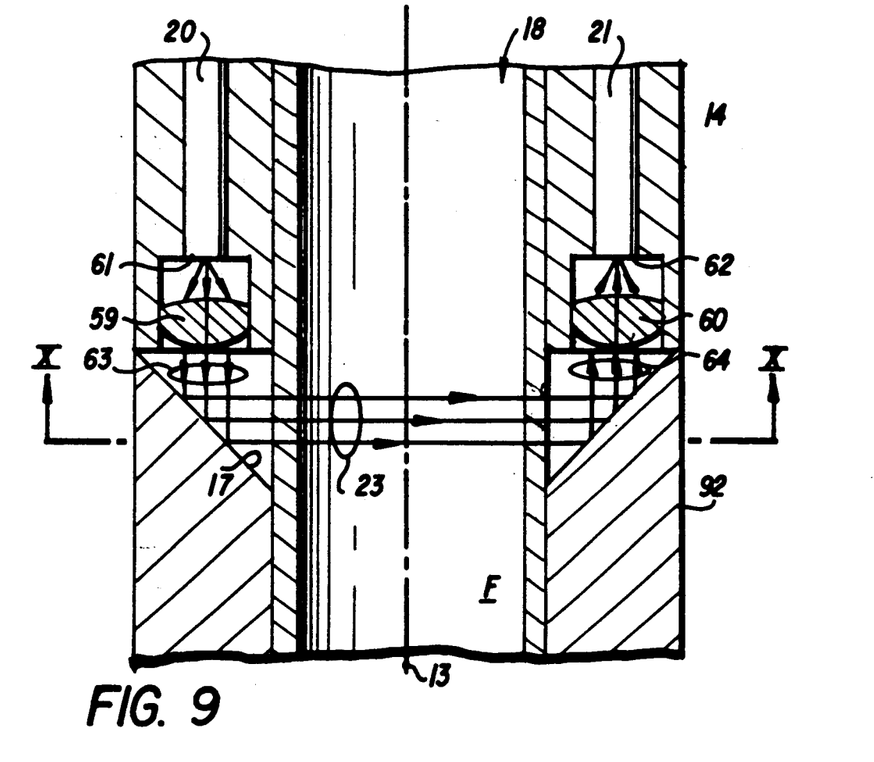
FIG. 9 illustrates an aspect of the invention in which lenses are employed to shape the light beam before and after reflection from the interior conical reflecting surface.
Figure 10:
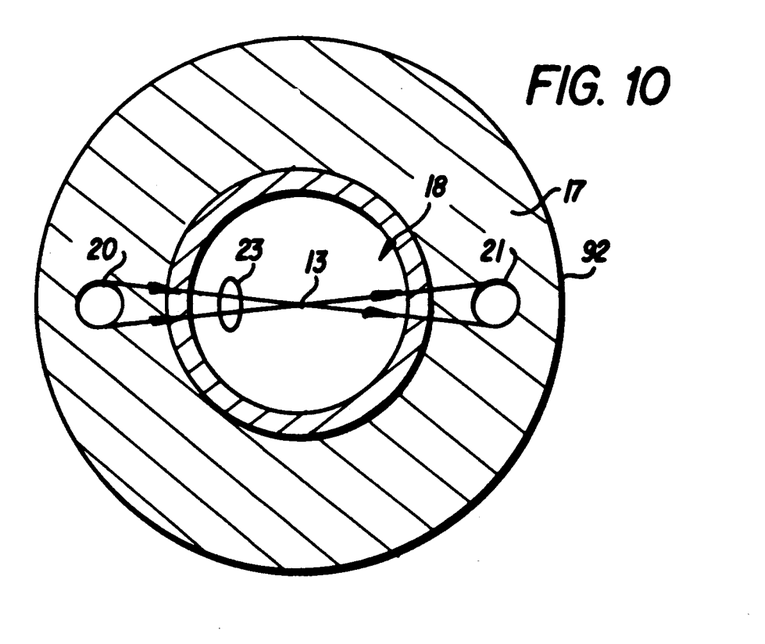
FIG. 10 illustrates another view of the apparatus of FIG. 9.

Specifically, the individual lenses 59, 60 are interposed between the ends 61, 62 of the light guides 20, 21, respectively. The lens 59 serves to substantially collimate the light leaving the light guide 20 and the collimated beam is in turn imaged (by the reflecting surface 17) at the center of the sample chamber 18, substantially independent of the index of refraction of the test fluid (F); this is shown even more clearly in FIG. 10, where the sampling light ray 23 is perpendicular to the axis of revolution 13 of the reflector segment 92. The incoming light rays and outgoing return light rays are represented collectively as light beam diameters 63, 64, respectively. The return light beam 64, incident on the lens 60 is re-imaged onto the end (i.e., input face) 62 of the light guide 21. The longitudinal line image, formed at the center line (or axis of revolution 13 of the reflector segment 92) of the sample chamber 18 has a length substantially equal to the diameter 63 (and also the diameter 64).

Figure 11:
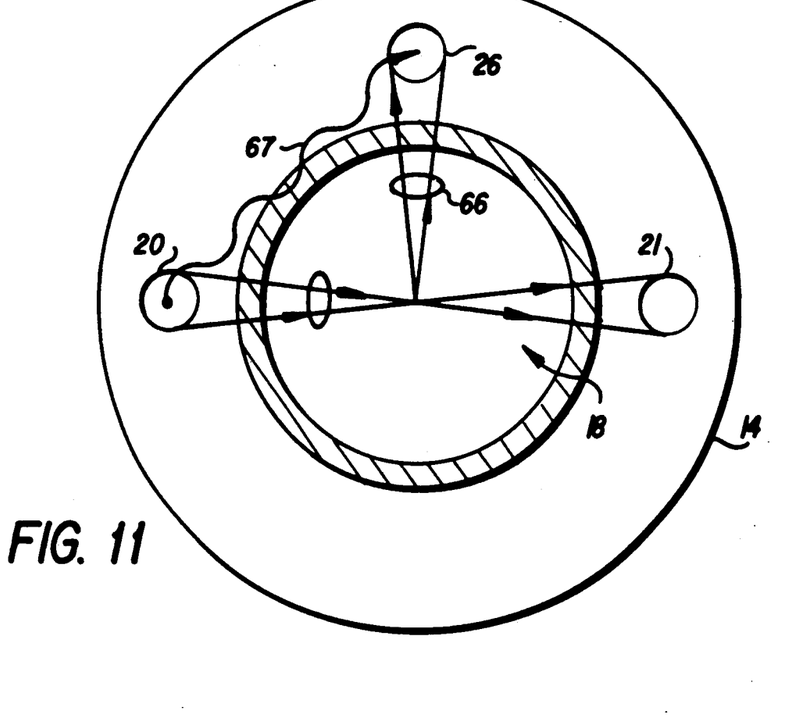
FIG. 11 illustrates in plan view another aspect of the invention which solves the potential problem of stray light.
Figure 12:
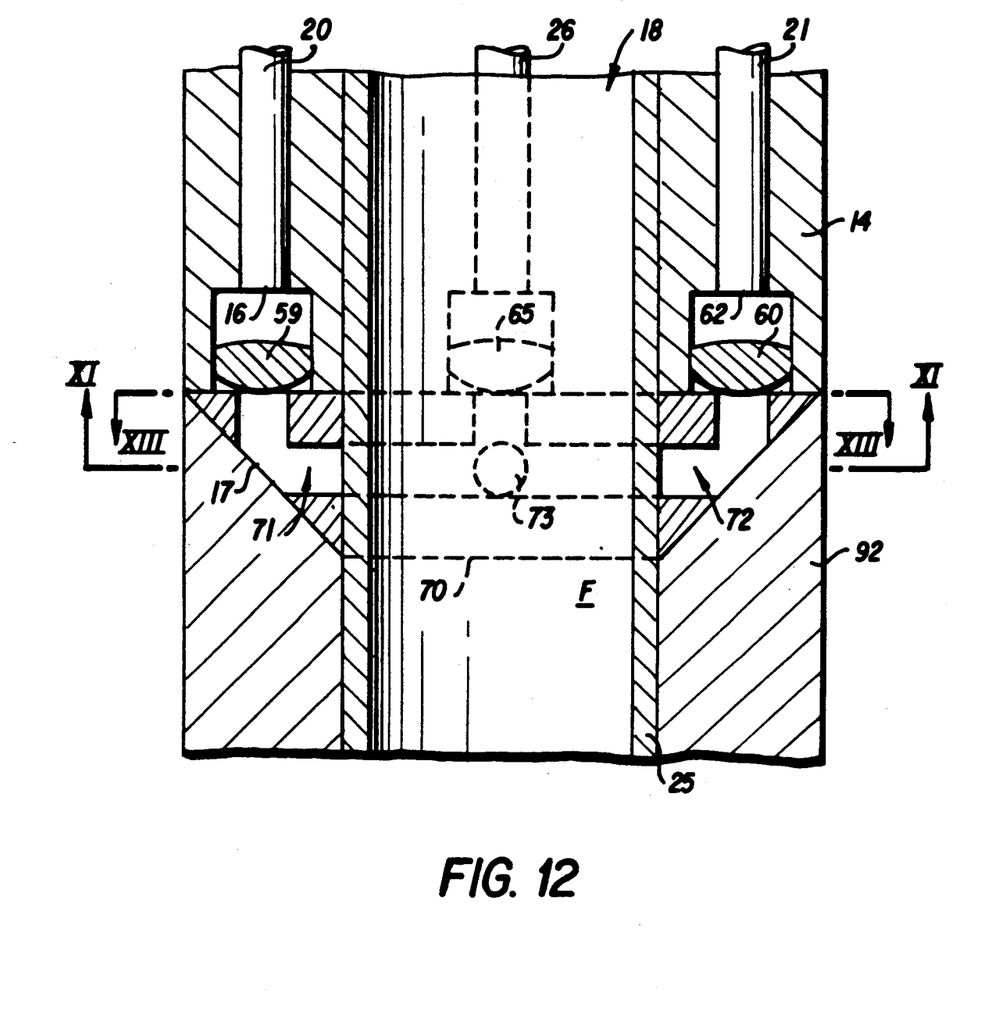
FIG. 12 illustrates in longitudinal section view the baffle of FIG. 11, incorporating apparatus similar to that of FIG. 2.
Figure 13:
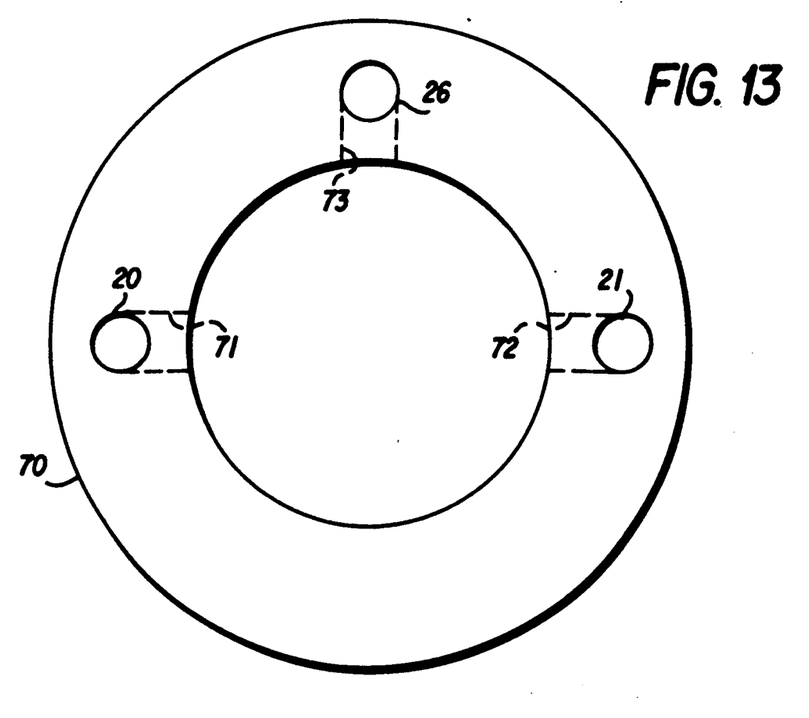
FIG. 13 illustrates another view of the baffle according to FIG. 11.

In certain uses it will be desirable to eliminate or reduce stray light. Those of skill in the art will appreciate that a limitation to many optical-based measurement systems is the presence of stray light, which by definition, is that light which reaches the detector by paths other than that intended. As an example, in turbidity measurements, excessive stray light may limit sensitivity when analyzing for low levels of suspended matter. One way to minimize sources of stray light in an optical probe is shown in FIGS. 11, 12, and 13. A stray light baffle 70 may be used to eliminate or reduce stray light. Such a baffle 70 limits the angle of passage of light through the test chamber 18 wall 25.

An additional light path via the lens 65 is positioned approximately normal to the optical axis (defined by the light ray 23 in FIGS. 2 and 9) and passing through the center of the sample chamber 18. This configuration may be employed for measuring very low turbidity levels, but may also be appropriate for Raman spectroscopy. A portion of the light scattered by matter in the sample fluid (F) volume near a point, for example the centerline and axis of revolution 13, is directed towards the collection lens 65. The light rays 66 comprise this light. Stray radiation such as that indicated by a wavy line light ray 67 may also reach the lens 65 if the conical reflecting surface 17 is not perfectly smooth, so that light incident upon it from the lens 59 may be scattered by surface defects into many directions, only one example of which is illustrated by the wavy line light ray 67. One of ordinary skill will appreciate that the light ray 67 does not actually travel in the curvilinear fashion indicated but rather is illustrative in nature. The presence of such rays reaching the collection lens 65 and from there via the light guide 26 to the appropriate detection means (not shown) implies that in the absence of any scattering material in the test chamber 18, a finite signal is produced. This signal, if large enough, can adversely limit the sensitivity of the device and make a precise measurement of low concentrations quite difficult.

To eliminate this difficulty, a circular light restricting baffle 70 including a plurality of radially extending passageways 71, 72, 73 is interposed between the reflective surface 17 of the reflector segment 92 and the main body segment 14, which latter segment contains the lenses 59, 60, 65 and the respective light guides. Baffle 70 includes a passageway 71, which permits light from light guide 20 to pass unobstructed into sample chamber 18 after collimation by lens 59. Another radial passageway 72 permits the directly transmitted beam to pass through unobstructed to the lens 60, and a third radial passageway 73 of the baffle 70 permits light scattered by the sample to pass on further to the lens 65. However, baffle 70 prevents stray light rays such as the stray ray 67 from reaching the lens 65 except via the baffle 70 passageways 71, 72, 73 and the sample chamber 18. A plan view of the baffle 70 is shown in FIG. 13. By varying the size and shape of the passageways created in the baffle 70, it is further possible to control such factors as how much light is collected by the lens 65 for purposes of controlling the collection angle of light.

Figure 14:
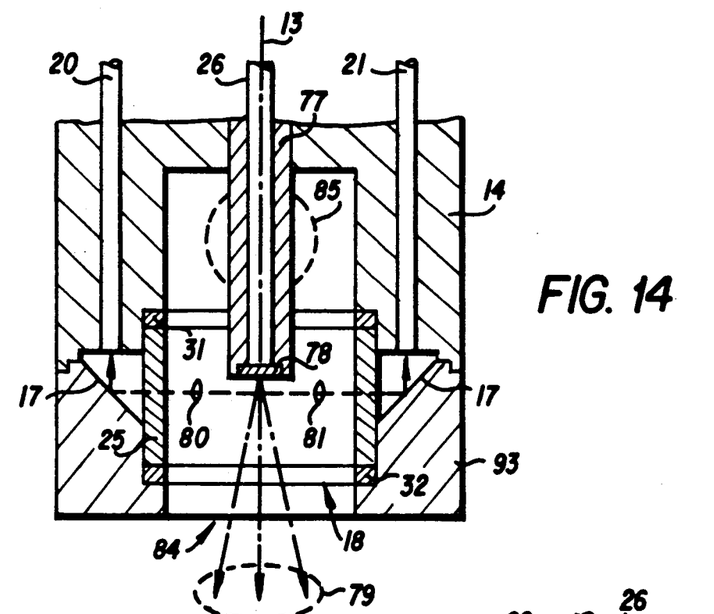
FIG. 14 illustrates an aspect of the invention in which radiant energy is introduced directly into a sample test chamber and scattered radiation is collected by the interior conical reflector element.

FIG. 14 illustrates yet another embodiment of the invention whereby light is introduced along the longitudinal central axis 13 of the cylindrical sample chamber 18; that light which is scattered at 90 degrees is collected by the reflecting surface 17 and directed towards one or more receiving light guides, illustrated by the light guides 20, 21. Here, the light guide 26, contained within a protective sheath 77 carries light to the sample chamber 18 where it passes through a protective, transparent window 78. The light beam 79 emerging from the window 78 is scattered at various angles. The assembly and construction of the configuration illustrated in FIG. 14 is substantially the same as that previously described except that the incoming light is introduced along the longitudinal axis and collected normal thereto. In particular, the light rays 80 and 81 illustrate light rays which have been scattered at about 90 degrees with respect to the incident light beam 79 by the test fluid (F). The approximately 90-degree scattered radiation is directed towards a plurality of collecting optical fibers 20, 21 by conical reflector segment 93 reflecting surface 17. Here, segment 93 is open-ended and truncated to permit free flow of the sample into the sample chamber. Again, the sample chamber 18 is disposed between the O-ring seals 31, 32 while a lower port 84 and an upper port 85 permit free exchange of test fluid (F) within the sample chamber 18. A lens could be interposed between the light guide 26 and the window 78 (or substituted for window 78) whereby the shape of the outgoing beam 79 could be adapted to a wide variety of measuring requirements; thus the point of maximum energy concentration within light beam 79 could be extended further beyond window 78 by suitable choice of lens power.

Figure 15:
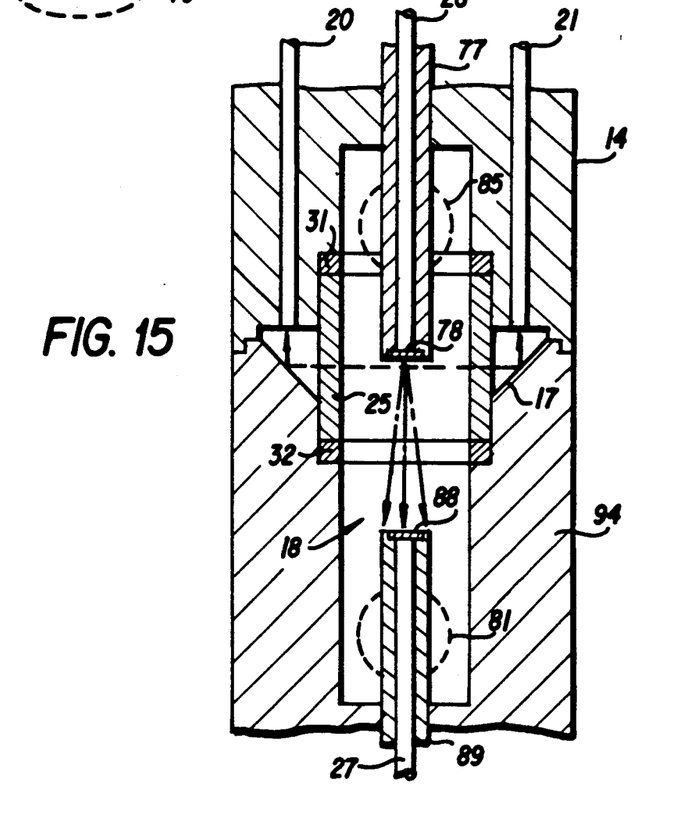
FIG. 15 illustrates alternative apparatus in which radiant energy is introduced directly into a sample test chamber and scattered radiation is collected by the interior conical reflector element.

A still further embodiment of this present invention is disclosed in FIG. 15, where light is introduced along the longitudinal axis and in which transmitted radiant energy may be collected by at least one additional light guide 27, as well as scattered light being collected by light guides 20, 21. In this case, the sample chamber 18 is self-contained and an additional port 87 is added to permit the test fluid (F) to flow through the sample chamber 18. The assembly and construction of the configuration illustrated in FIG. 15 is substantially the same as that previously described. Reflective segment 94, however, is closed below port 87.

Thus, as described above, this invention provides a method and apparatus for simplifying the introduction of light into and from a sample chamber for the purposes of monitoring changes in the transmitted, attenuated, or scattered radiant energy passed through the sample chamber.

The invention is not to be limited by the illustrative, preferred embodiments disclosed herein. Numerous modifications and variations will be apparent to those skilled in the art. Other equivalent light communications pathways may be employed; equivalent materials may be substituted; and equivalents of the particular methods of forming parts disclosed may be employed without departing from the spirit and scope of the present invention as claimed in the appended claims.

I claim:

1. In an optical sensing system including a source of radiant energy and an optical detector, a probe for optical sampling comprising:
   (a) a chamber having an optical entry and an optical exit and a fluid port,
   (b) means for directing radiant energy from said source into and through said chamber to an exit;
   (c) means for collecting said radiant energy exiting from said chamber;
   (d) first pathway means for conveying radiant energy to said means for directing radiant energy through said chamber; and
   (e) second pathway means for conveying radiant energy away from said chamber exit to said detector,
   (f) means for sealing said fluid port and providing thereby a stilling well;
   wherein said means for directing radiant energy into and through said chamber to said exit and said means for collecting radiant energy comprise surface portions of an interior conical reflecting surface.

2. The probe of claim 1, wherein said chamber contains a liquid, and said radiant energy is directed through said liquid.

3. The probe of claim 1, further including means for admitting successive fluid samples through said chamber.

4. The probe of claim 1, further including an optical lens element between said first pathway and said means for directing.

5. The probe of claim 1, further including an optical lens element between said second pathway and said means for collecting.

6. The probe of claim 1, wherein said radiant energy wavelength is between $1 \times 10^{-7}$ and $1 \times 10^{-4}$ meters.

7. The probe of claim 1, further including a baffle having at least one light-passage pathway therethrough, said baffle being disposed between said means for directing radiant energy and said chamber.

8. The probe of claim 1, further including a baffle having at least one light-passage pathway therethrough, said baffle being disposed between said means for collecting radiant energy and said chamber.

9. The probe of claim 1, wherein said chamber includes a light transmissive tubular wall.

10. The probe of claim 1, further including a radial flange.

11. The probe of claim 1 having a longitudinal axis and at least one means for directing radiant energy from said source into and through said chamber to an exit and at least one means for collecting said radiant energy exiting from said chamber, wherein the radiant energy from said source directed into said chamber and the radiant energy exiting from said chamber are perpendicular to said longitudinal axis.

12. The probe of claim 1 having a longitudinal axis and at least one means for directing radiant energy from said source into and through said chamber to an exit and at least one means for collecting said radiant energy exiting from said chamber, wherein the radiant energy from said source directed into said chamber and the radiant energy exiting from said chamber are diametrically opposed perpendicular to said longitudinal axis.

13. The probe of claim 1 having a longitudinal axis and at least one means for directing radiant energy from said source into and through said chamber to an exit and at least one means for collecting said radiant energy exiting from said chamber, wherein the radiant energy from said source directed into said chamber and the radiant energy exiting from said chamber are perpendicular to said longitudinal axis and are also disposed at about right angles to one another.

14. In a probe for optical sampling of a fluid in a chamber having an optical entry and an optical exit and first and second fluid ports, the method of optical sampling comprising:
   (a) providing radiant energy from a source of radiant energy;
   (b) conveying radiant energy via a first pathway means to means for directing radiant energy through the chamber;
   (c) directing the radiant energy from said pathway into and through said chamber to an exit by reflection from a surface portion of an interior conical reflector;
   (d) collecting said radiant energy exiting from said chamber by reflection from a surface portion of an interior conical reflector;
   (e) conveying radiant energy via a second pathway means away from said chamber exit; and
   (f) sealing at least one of said fluid ports for a sufficient period of time for the fluid to become stilled.

15. The method of claim 14, wherein said chamber contains a fluid, and the further step of directing radiant energy through said fluid.

16. The probe of claim 14, further including the step of admitting successive fluid samples through said chamber.

17. The probe of claim 14, further including the step of passing the light through an optical lens element between said first pathway and said means for directing.

18. The method of claim 14 wherein said probe includes a baffle having at least one light-passage pathway therethrough, said baffle being disposed between said means for directing radiant energy and said chamber, further characterized by limiting the light passage to said baffle passageways during the step of conveying radiant energy into the chamber.

19. The method of claim 14 wherein said probe includes a baffle having at least one light-passage pathway therethrough, said baffle being disposed between said means for collecting radiant energy and said chamber, further characterized by limiting the light passage to said baffle passageways during the step of collecting radiant energy from the chamber.

20. In an optical sensing system including a source of radiant energy and an optical detector, a probe for optical sampling of a fluid in a chamber having an optical entry and an optical exit, comprising:
   (a) means for directing radiant energy from said source into and through said chamber to said exit;
   (b) first pathway means for conveying radiant energy to said means for directing radiant energy through said chamber;
   (c) means for collecting said radiant energy exiting from said chamber; and
   (d) second pathway means for conveying radiant energy away from said chamber exit to said detector,
   wherein said means for directing radiant energy into and through said chamber to said exit and said means for collecting radiant energy comprise partial surfaces of at least one interior conical reflecting surface.

21. The probe of claim 20, wherein said chamber contains a liquid, and said radiant energy is directed through said liquid.

22. The probe of claim 20, further including means for moving successive fluid samples through said chamber.

23. The probe of claim 20, further including an optical lens element between said first pathway and said means for directing.

24. The probe of claim 20, further including an optical lens element between said second pathway and said means for collecting.

25. The probe of claim 20, wherein said radiant energy wavelength is between $1 \times 10^{-7}$ and $1 \times 10^{-4}$ meters.

26. The optical system of claim 20, further including a baffle having at least one light-passage pathway therethrough, said baffle being disposed between said means for directing radiant energy and said chamber.

27. The optical system of claim 20, further including a baffle having at least one light-passage pathway therethrough, said baffle being disposed between said means for collecting radiant energy and said chamber.

28. The optical system of claim 20, wherein said chamber includes a light transmissive tubular wall.

29. The optical system of claim 20, further including a radial flange.

30. The optical system of claim 20 having a longitudinal axis and at least one means for directing radiant energy from said source into and through said chamber to an exit and at least one means for collecting said radiant energy exiting from said chamber, wherein the radiant energy from said source directed into said chamber and the radiant energy exiting from said chamber are perpendicular to said longitudinal axis.

31. The optical system of claim 20 having a longitudinal axis and at least one means for directing radiant energy from said source into and through said chamber to an exit and at least one means for collecting said radiant energy exiting from said chamber, wherein the radiant energy from said source directed into said chamber and the radiant energy exiting from said chamber are diametrically opposed perpendicular to said longitudinal axis.

32. The optical system of claim 20 having a longitudinal axis and at least one means for directing radiant energy from said source into and through said chamber to an exit and at least one means for collecting said radiant energy exiting from said chamber, wherein the radiant energy from said source directed into said chamber and said radiant energy exiting from said chamber are perpendicular to said longitudinal axis and are also disposed at about right angles to one another.

33. In a probe for optical sampling of a fluid in a chamber having an optical entry and an optical exit, the method of optical sampling comprising:
(a) providing radiant energy from a source of radiant energy;
(b) conveying radiant energy via a first pathway means to means for directing radiant energy through the chamber;
(c) directing the radiant energy from said source into and through said chamber to an exit with partial surfaces of an interior conical reflector;
(d) collecting said radiant energy exiting from said chamber; and
(e) conveying radiant energy via second pathway means away from said chamber exit.

34. The method of claim 33, wherein said chamber contains a fluid, and the further step of directing radiant energy through said fluid.

35. The probe of claim 33, further including the step of admitting successive fluid samples through said chamber.

36. The probe of claim 33, further including the step of passing the light through an optical lens element between said first pathway and said means for directing.

37. The method of claim 33 wherein said probe includes a baffle having at least one light-passage pathway therethrough, said baffle being disposed between said means for directing radiant energy and said chamber, further characterized by limiting the light passage to said baffle passageways during the step of conveying radiant energy into the chamber.

38. The method of claim 33 wherein said probe includes a baffle having at least one light-passage pathway therethrough, said baffle being disposed between said means for collecting radiant energy and said chamber, further characterized by limiting the light passage to said baffle passageways during the step of collecting radiant energy from the chamber.

39. A light reflecting optical probe element for optical sampling of a fluid in a chamber having an optical entry and an optical exit, comprising:
(a) means for directing light into and through said chamber to an exit; and
(b) means for collecting light exiting from said chamber;
wherein said means for collecting light exiting said chamber comprises at least one surface portion of an interior reflecting conical surface.

40. The probe of claim 39, wherein said chamber contains a fluid, and said radiant energy is directed into said fluid.

41. The probe of claim 39, further including means for admitting successive fluid samples through said chamber.

42. The probe of claim 39, further including a baffle having at least one light-passage pathway therethrough, said baffle being disposed between said means for collecting radiant energy and said chamber.

43. The probe of claim 39, wherein said chamber includes a light transmissive tubular wall.

44. The probe of claim 39, further including a radial flange.

45. The probe of claim 39 having a longitudinal axis and at least one means for directing radiant energy from said source into and through said chamber to an exit and at least one means for collecting said radiant energy exiting from said chamber, wherein the radiant energy exiting from said chamber is perpendicular to said longitudinal axis.

* * * * *